(12) United States Patent
Flanders

(10) Patent No.: US 9,110,041 B2
(45) Date of Patent: Aug. 18, 2015

(54) SELF-TESTING COMBUSTIBLE GAS AND HYDROGEN SULFIDE DETECTION APPARATUS

(75) Inventor: Patrick S. Flanders, Houston, TX (US)

(73) Assignee: Aramco Services Company, Houston, TX (US)

(*) Notice: Subject to any disclaimer, the term of this patent is extended or adjusted under 35 U.S.C. 154(b) by 600 days.

(21) Appl. No.: 13/198,155

(22) Filed: Aug. 4, 2011

(65) Prior Publication Data
US 2013/0031953 A1    Feb. 7, 2013

(51) Int. Cl.
*G01N 33/00*    (2006.01)

(52) U.S. Cl.
CPC .......... *G01N 33/0006* (2013.01); *G01N 33/007* (2013.01); *G01N 33/0044* (2013.01)

(58) Field of Classification Search
CPC .......... G01N 33/0006; G01N 27/4163; G01N 2033/0072; G01N 33/004
USPC .................. 73/1.01, 1.02, 1.03, 23.21, 23.31, 73/31.01, 31.02
See application file for complete search history.

(56) References Cited

U.S. PATENT DOCUMENTS

| | | | |
|---|---|---|---|
| 3,882,477 A | 5/1975 | Mueller | |
| 4,094,187 A * | 6/1978 | Navarre, Jr. | 73/863.83 |
| 4,177,381 A | 12/1979 | McClatchie et al. | |
| 4,322,964 A * | 4/1982 | Melgaard et al. | 73/1.06 |
| 4,384,925 A * | 5/1983 | Stetter et al. | 205/785.5 |
| 4,854,153 A * | 8/1989 | Miyagawa et al. | 73/1.06 |
| 5,086,642 A | 2/1992 | Jessel et al. | |
| H1676 H * | 9/1997 | Marshall | 340/605 |
| 5,734,116 A * | 3/1998 | Schaeffer | 73/865.6 |
| 5,797,358 A * | 8/1998 | Brandt et al. | 122/448.1 |
| 5,945,924 A * | 8/1999 | Marman et al. | 340/928 |
| 6,135,100 A * | 10/2000 | Katoh | 123/679 |
| 6,169,488 B1 * | 1/2001 | Ketler | 340/632 |
| 6,451,606 B1 * | 9/2002 | Konig et al. | 436/8 |
| 6,454,923 B1 | 9/2002 | Dodgson et al. | |
| 6,611,208 B1 * | 8/2003 | Ketler | 340/632 |
| 6,629,444 B2 | 10/2003 | Peng | |
| 6,632,674 B1 * | 10/2003 | Warburton | 436/8 |
| 6,772,598 B1 * | 8/2004 | Rinehart | 62/126 |
| 6,997,347 B2 | 2/2006 | Peng et al. | |
| 7,017,386 B2 | 3/2006 | Liu et al. | |
| 7,041,256 B2 | 5/2006 | Wang et al. | |

(Continued)

FOREIGN PATENT DOCUMENTS

GB    2219403 A    6/1989
WO    WO 9801709 A2 *    1/1998

OTHER PUBLICATIONS

PCT International Search Report mailed on Oct. 31, 2012.

*Primary Examiner* — David A Rogers
(74) *Attorney, Agent, or Firm* — Bracewell & Giuliani LLP; Constance Gall Rhebergen

(57) ABSTRACT

An automated testing apparatus for remotely performing a testing sequence to ensure that a sensor is functioning. The apparatus can include a detector, a storage container, a burst valve in fluid communication with the storage container, a testing control module in communication with the storage container and the burst valve, and a remote user interface remotely located from the detector. Preferably, the automated testing apparatus can simplify the testing procedure, increase the frequency of sensor testings, thereby notifying operations of sensor failures in a more timely fashion without the need for an operator to check the sensor locally.

26 Claims, 4 Drawing Sheets

(56) References Cited

U.S. PATENT DOCUMENTS

| | | |
|---|---|---|
| 7,062,952 B2 | 6/2006 | Gokhfeld |
| 7,174,766 B2 * | 2/2007 | Eickhoff et al. ............... 73/1.03 |
| 7,242,288 B2 | 7/2007 | Kaiser et al. |
| 7,530,255 B2 | 5/2009 | Frank et al. |
| 7,640,783 B2 * | 1/2010 | Eickhoff ........................ 73/1.06 |
| 7,655,186 B2 | 2/2010 | Tobias |
| 7,661,290 B2 * | 2/2010 | Gu et al. ........................ 73/1.03 |
| 7,704,356 B2 * | 4/2010 | Kuhn ........................... 204/401 |
| 7,878,258 B2 * | 2/2011 | Lindstrom et al. ............... 169/61 |
| 7,937,984 B2 * | 5/2011 | Tobias ........................... 73/1.06 |
| 7,951,273 B2 * | 5/2011 | Caro et al. .................. 204/230.2 |
| 8,117,886 B2 * | 2/2012 | Rolff et al. ..................... 73/1.02 |
| 8,220,308 B2 * | 7/2012 | Bellis et al. .................... 73/1.06 |
| 2003/0145644 A1 * | 8/2003 | Rabbett et al. ................. 73/1.06 |
| 2004/0055359 A1 | 3/2004 | Ketler |
| 2005/0000981 A1 * | 1/2005 | Peng et al. ........................ 222/3 |
| 2005/0100478 A1 | 5/2005 | Harvey |
| 2005/0135970 A1 | 6/2005 | Mroczynski et al. |
| 2005/0262924 A1 * | 12/2005 | Wood et al. .................. 73/31.05 |
| 2008/0156071 A1 | 7/2008 | Tobias |
| 2008/0159917 A1 | 7/2008 | Tobias |
| 2008/0282765 A1 | 11/2008 | Bonne et al. |
| 2010/0081909 A1 * | 4/2010 | Budiman et al. ............... 600/365 |

* cited by examiner

SELF-TESTING COMBUSTIBLE GAS AND HYDROGEN SULFIDE DETECTION APPARATUS

TECHNICAL FIELD OF THE INVENTION

The present invention relates to a method and apparatus for safely ensuring the functionality of combustible gas and hydrogen sulfide detectors.

BACKGROUND OF THE INVENTION

Within many operating facilities and well sites, fixed gas detection systems are deployed to warn employees of a dangerous release of hydrogen sulfide or combustible gases. However, the sensors used within the fixed detectors can become disabled or "poisoned" over time. In this state, although the sensor has lost sensitivity to the targeted gas, the detector appears to otherwise operate normally. To test for this failure of sensitivity, field level calibrations are conducted on a regular basis.

Within operations, a full calibration test interval is generally prescribed at a minimum of 90 days, with an interval of 30 days for some higher risk applications. Conventional methods require the external application of target gas using a jar with glass ampoules or with a portable calibration gas cylinder. The process is performed manually at the site of the sensor, which is typically a site of increased risk for exposure to hazardous gaseous emissions, thereby necessitating the placement of the sensor to monitor conditions. As such, the standard method is time consuming and puts the employee performing the calibrations at risk for operational hazards.

Currently, those charged with maintaining the sensors are also the primary recording source for tagging the sensor indicating the date of the last test and for reporting a testing failure. Thus, if the operator fails to take these actions and report that a sensor is not fully functional, then no record is kept, and no action is taken. Similarly, weathering can degrade the ability to review manual markings of testing dates.

Therefore, there is a need for a device that can test the detectors while reducing the risk to the employee. Additionally, there is a need for a device that can test the detectors more frequently and faster, such as through an automated process, and thereby streamline the overall process. Similarly, it would be advantageous to create a system that records conditions of sensors at each test using a method that minimizes environmental degradation and provides specific information suitable to audit the history of each sensor and thereby the entire safety system of sensors.

Therefore, it would be desirable to have an improved apparatus for ensuring that these vital safety devices are still functioning. It would also be desirable if the apparatus could alert operations when dangerous faults are detected in "real time" as they occur rather than remaining undetected with the sensor in a disabled state until the next scheduled test. Preferably, it would be desirable to have an apparatus that did not require the use of large amounts of manpower to perform these tests. Additionally, it would be beneficial if the apparatus could be implemented with existing infrastructure.

SUMMARY OF THE INVENTION

The present invention is directed to an apparatus that satisfies at least one of these needs. The invention includes an automated testing apparatus that is operable to perform a testing sequence to determine whether or not a sensor is functioning as desired. In one embodiment, the automated testing apparatus for detection of a chemical substance can include a detector, a storage container, a burst valve assembly, a testing control module, and a remote user interface. In one embodiment, the detector includes a sensor that is operable to detect the presence of the chemical substance. Exemplary chemical substances include combustible gas, hydrogen sulfide, carbon monoxide, and other toxic or poisonous gaseous substance.

In another embodiment, the storage container is operable to store a testing material. In one embodiment, the testing material is a gas when released at atmospheric conditions. Exemplary testing material includes combustible gas, hydrogen sulfide, carbon monoxide, and combinations thereof. Those of ordinary skill in the art will recognize that the chosen testing material will vary depending on the chemical substance that is being detected by the sensor.

In another embodiment, the burst valve assembly is in fluid communication with the storage container. In one embodiment, the burst valve assembly can include a burst valve, with the burst valve being operable to control an amount of the testing material released from the storage container through the burst valve assembly such that the burst valve assembly is operable to deliver a quantity of the testing material through the burst valve assembly. The amount of the testing material to be applied to the sensor is lower than an amount that would poison or desensitize the sensor to be tested. In an additional embodiment, the amount of testing material applied is lower than an amount that would be applied during a full calibration test, thereby reducing the potential for desensitizing the sensor. In one embodiment, the burst valve assembly is positioned in relation to the sensor such that the burst valve assembly is operable to deliver the quantity of testing material in close proximity to the sensor, such that the testing material can be detected by the sensor.

In another embodiment, the testing control module is in communication with the burst valve assembly. In one embodiment, the testing control module is operable to provide a signal to activate the burst valve and to initiate flow of the testing material from the storage container through the burst valve assembly. Communication between the testing control module and the burst valve assembly can be made by means known in the art, including hard wiring such as an interconnecting cable and/or radio frequency transmission.

In another embodiment, the remote user interface can be located remotely from the detector. In one embodiment, the remote user interface is in communication with the testing control module, wherein the remote user interface is operable to receive a detection signal from the testing control module and output a discernable signal that is operable to indicate whether the sensor is functioning. In another embodiment, the discernable signal is operable to indicate the presence of a fault within the detector.

In another embodiment, the remote user interface can further include an input/output device, a computer, and a program product. In one embodiment, the input/output device is operable to interact with the user. In an additional embodiment, the computer defines a signal processing device having non-transitory computer memory, wherein the computer is in electronic communication with the input/output device and the testing control module. In one embodiment, the signal processing device is operable to receive and transmit instructions between the input/output device and the testing control module. In an additional embodiment, the program product can be stored in memory and operable on the signal processing device. In one embodiment, the program product is in electronic communication with the signal processing device.

In another embodiment, the program product can be composed of instructions executable for initiating a testing sequence, wherein the testing sequence includes the steps of delivering the testing material through the burst valve assembly in close proximity to the sensor, sensing the presence of the testing material by the sensor, and receiving a signal from the sensor to the testing control module indicating whether the sensor detected the presence of the testing material.

In an additional embodiment, the testing control module can store diagnostic data from the testing sequence. In one embodiment, the diagnostic data can include timestamps for each testing sequence conducted, testing sequence results, and the length of time between receipt of the test result from the sensor and occurrence of a designated response, wherein the test result indicates a failure of the sensor to detect the presence of the testing material.

In another embodiment, the remote user interface is located within a control room, such that the remote user interface can be accessed in a location away from the hazardous condition. In one embodiment, the automated testing apparatus can also include means for measuring the pressure of the testing material within the storage container, and means for calculating the amount of testing material flowing through the burst valve assembly based on the amount of time the burst valve is in an open position and the pressure difference of the storage container between a closed position and the open position of the burst valve. The means for measuring the pressure of the testing material can be done with devices known to those of ordinary skill in the art.

In an embodiment where the amount of testing material is calculated, this provides a detailed basis for calibration of the sensor without involving maintenance personnel. This allows for more frequent calibration at a fraction of the cost compared to manual calibration. This also eliminates the needs for mobile calibration equipment that the operators take to the site of the sensor to be calibrated, thus reducing overall equipment cost.

In an embodiment where the amount of testing material is generally maintained below the level that would impact sensor effectiveness but not discretely determined, the testing control module would be suitable for determining whether or not the sensor being tested is desensitized. In one embodiment, testing for desensitization can be done by time by comparing the results of repeated tests.

In another embodiment, the testing control module can also include a pressure monitoring system in communication with the burst valve, wherein the pressure monitoring system is operable to monitor the pressure of the storage container. In one embodiment, the pressure monitoring system is in pneumatic communication with the burst valve. In another embodiment, the pressure monitoring system can include a gauge in communication with the storage container. In one embodiment, the present invention can also include means for determining the amount of testing material within the storage container. In another embodiment, the present invention can alert operations when additional testing material is needed.

In another embodiment, the testing control module can also include internal memory that is operable to store diagnostic data. In one embodiment, the diagnostic data includes timestamps for each testing sequence conducted, testing sequence results, and length of time between receipt of the test result from the sensor and occurrence of a designated response, wherein the test result indicates a failure of the sensor to detect the presence of the testing material. In one embodiment, the present invention can also include means for protecting the internal memory from dangerous conditions proximate to the sensor. Additionally, in one embodiment, the internal memory is operable to store instructions that can be initiated through the user interface panel locally placed within a detector housing, or mounted to the detector housing.

Detectors useful in the invention include a solid-state diffusion adsorption detector, a catalytic bead-type diffusion detector, a smoke detector, a carbon monoxide detector or the like. Infra-red detectors are also useful in the invention although catalyst poisoning is not of concern with this type of detector. Infra-red detectors can still malfunction so they can be tested using the current invention to determine if they are working properly.

In one embodiment, the present invention can further include the user interface panel in communication with the testing control module. In one embodiment, the user interface panel can allow for manual operation of the testing control module. In one embodiment, the user interface panel is located in a non-hazardous location remote from the testing control module. In another embodiment, the user interface panel is proximate to the testing control module. In another embodiment, the user interface panel can include a local test function switch that is operable to initiate a testing sequence for the automated testing apparatus. In another embodiment, the user interface panel further includes an indicator, wherein the indicator is selected from the group consisting of a failed test indicator, warning condition indicator, critical condition indicator, or combinations thereof.

In one embodiment, the burst valve assembly is operable to deliver the testing material to the sensor without a pump or compressed air supply. In another embodiment, the present invention can further include a sensor diffuser, wherein the sensor is disposed within the sensor diffuser. In one embodiment, the sensor diffuser contains a plurality of openings, that are operable to allow for air to flow through the sensor diffuser. In one embodiment, the plurality of openings can have various types of geometries. In one embodiment, the sensor diffuser is operable to promote a uniform distribution of the target material to the sensor.

In one embodiment, the burst valve can include a three-way valve, such that the testing control module is in fluid communication with the burst valve. In another embodiment, the present invention can further include a TCM-burst valve line in communication with the testing control module and the burst valve. In one embodiment, the TCM-burst valve line is operable to send a signal from the testing control module to the burst valve assembly to change a state of the burst valve.

In one embodiment, the present invention can also include a supplemental storage container in fluid communication with the storage container and the burst valve assembly, wherein the supplemental storage container operable to reduce the pressure exerted on the burst valve assembly due to the testing material.

In another embodiment, the supplemental storage container has an internal volume greater than the internal volume of the storage container.

In another embodiment, the present invention can also include a field connector, and the supplemental storage container can also include outer threads and a seat. The field connector can have inner threads that are operable to engage the outer threads of the supplemental storage container, such that when the inner threads engage with the outer threads, a threaded connection can be formed between supplemental storage container and the field connector. This threaded connection is operable to cause a downward force to be exerted on the storage container, such that the storage container engages with the seat and forming the fluid communication with the supplemental storage container.

In another embodiment, when the field connector is reverse threaded (i.e., removed), the storage container can be replaced with another full storage container. The seat can be spring loaded to isolate the supplemental storage container during replacement of the spent storage container. This provides a simple, convenient and reliable method of making replacements of the storage containers in the field where the detector is located.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
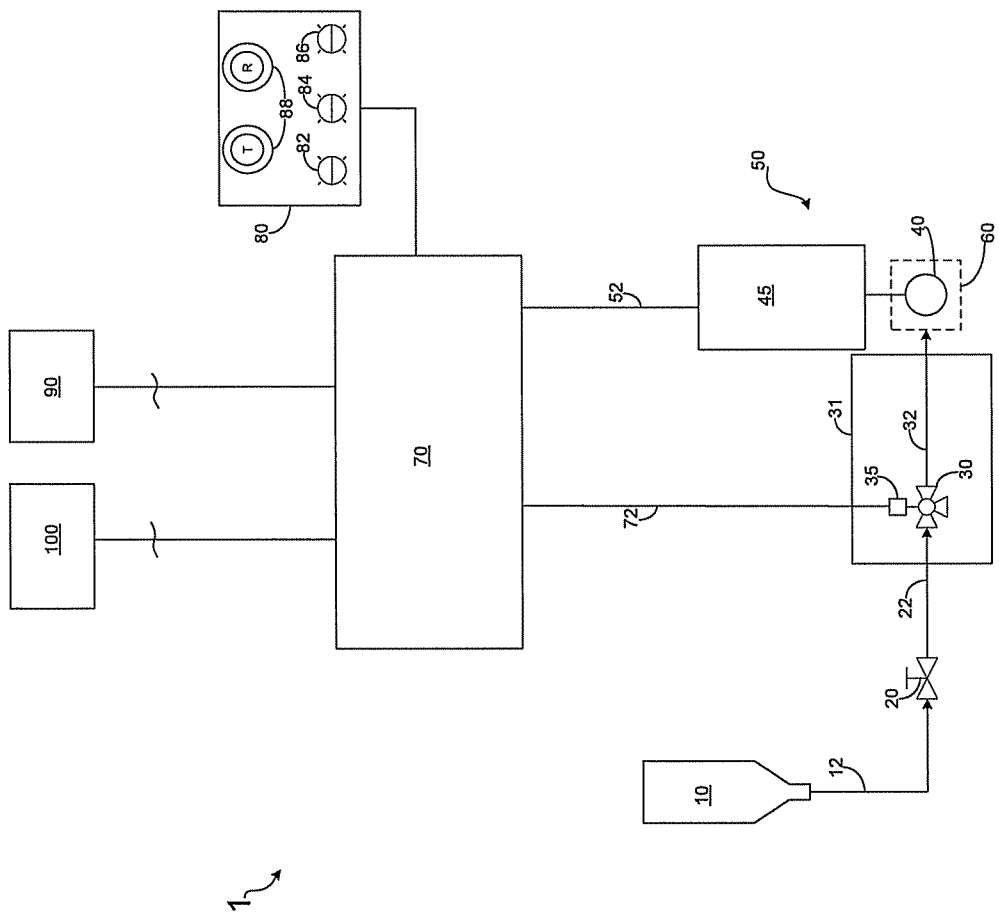
FIG. 1 is a representation of an embodiment of the present invention.

While the invention will be described in connection with several embodiments, it will be understood that it is not intended to limit the invention to those embodiments. On the contrary, it is intended to cover all the alternatives, modifications and equivalence as may be included within the spirit and scope of the invention defined by the appended claims.

In one embodiment, the automated testing apparatus for detecting the chemical substance is in a fixed location and can include the sensor, the storage container, the burst valve assembly in fluid communication with the storage container, and the testing control module in communication with the burst valve assembly. The automated testing apparatus acts to notify operations of sensor failures or calibration issues in a timely fashion, and without the need for a manual check of the sensor locally. In an additional embodiment, the automated testing apparatus is operable to test the ability of fixed gas detectors to properly detect and respond to hazardous concentrations of hydrogen sulfide and/or combustible gas-in-air monitoring systems by integrating testing control and calibration gas locally with the detectors. Advantageously, certain embodiments of the present invention will allow for automated or semi-automated on-line functional testing of the detectors, and therefore, improve the ability to detect dangerous, hidden failures, as well as the ability to take corrective maintenance action before a dangerous gas release occurs. In one embodiment, such testing of detectors is accomplished without disabling the system or causing a shutdown of equipment related to the monitoring of the sensor.

In additional embodiments, the present invention can deliver the testing material to the sensor without the need for internal pumps or an external compressed air supply. The amount of the testing material to be applied to the sensor is lower than an amount that would poison or desensitize the sensor to be tested. In another embodiment, the amount of the testing material to be applied to the sensor is lower than an amount that would be used during full calibration, thereby reducing the chance of desensitizing the sensor to be tested. In one embodiment, the testing material in the storage container has a concentration of the chemical substance operable to be exposed directly to the sensor without dilution. In an alternate embodiment, the concentration in the storage container is defined by an elevated concentration of the chemical substance and is diluted with air or non-combustible gases prior to exposure to the sensor. The air useful for dilution can be ambient air or can be provided separately, thereby allowing for discrete measurements and determination of concentrations for purposes of calibration. After exposure to the sensor, the chemical substance can be vented or removed from the area by other means known in the art. When using ambient air, one embodiment includes enhancing the circulation of the air present through the use of a pump or fan to increase dilution as compared to dilution occurring upon mixing with ambient air already present around the sensor or to establish a preferred flow pattern.

Testing can be initiated and monitored from a safe and convenient location that is remote from the hazardous location where the sensor is located. The remote initiation capability can be combined with a local testing initiation capability at the location of the sensor, if appropriate under the environmental circumstances. In additional embodiments, the present invention can also include a sensor diffuser that surrounds the sensor and allows for ambient air to mix with the released testing material. In another embodiment, the present invention can also include local memory, which can record diagnostic data, such as time stamping of testing sequences, test results, and elapsed time from fault detection to repair. The diagnostic data, whether saved locally or remotely, provides accountability tools since the data can be audited at a later date to ensure operators are implementing best practices in safety protocol and can allow for optimization of safety procedures related to sensors, typically monitored by Loss Prevention or Health and Safety professionals. Simultaneously, the automated aspects of the testing apparatus free operator personnel from spending time on sensors that are working properly and allow them to focus on only those sensors requiring maintenance or other critical issues in the plant, thus creating a more efficient workforce. Additionally, a history of fault detection on specific sensors, including time stamps, is a diagnostic tool to assist in determination of a faulty sensor that should be replaced, reoccurring poisoning of sensor leading to equipment analysis or other potential maintenance problems.

Fault detection results in communication of the fault or failure or alternatively, the passing of the test. Warning alarm or critical (high) alarm levels can be used. Such alarms can be visual alarms, audible alarms and/or any other useful sensory alert and can be in the field as well as in the control room, or forwarded to pagers, cell phones, electronic mail, or the like. In certain instances, such as when control rooms are unattended, alarms can be posted at the entrance gates. In one embodiment, alarm reset includes re-testing after correction of the fault to ensure correction of the fault and avoidance of unauthorized system bypass or unauthorized alarm reset. Data sent to the control room can also identify the specific sensor that is in a failed state and can identify the location of that sensor.

In certain embodiments, the diagnostic data can be automatically input into an asset management system implemented for the facility. Alternately, the automated testing apparatus of the invention can be used in place of an asset management system for sensors incorporated into the automated testing apparatus in accordance with the invention as instructions can be stored directly indicating automatic initiation of the testing sequence on a specific date and storing of the diagnostic data resulting from the testing sequence, including "check sensor" status alerts for sensors that fail the test. Thus, the tags for sensors that form part of the automated testing apparatus of the current invention are actively monitored in a manner permitting audit without registering such tags into the asset management system.

In another embodiment, the diagnostic data can be recorded locally within the testing control module's internal memory and additionally communicated to a separate location, such as the control room or the remote user interface. In an additional embodiment, the diagnostic data can be protected from an explosion or other catastrophic plant occurrence so that the previously recorded diagnostic data can be accessed during a subsequent incident investigation.

FIG. 1 shows one embodiment of the invention. Automated testing apparatus 1 can include storage container 10, which is useful for storing testing material. Non-limiting examples of acceptable devices suitable for use as storage container 10 can include, for example miniature one-piece cylinders filled under pressure, or the like. Automated testing apparatus 1 can also optionally include isolation valve 20, which is useful for isolating storage container 10 from the rest of automated testing apparatus 1. Burst valve 30, which forms part of burst valve assembly 31, is in fluid communication with storage container 10 via lines 12, 22. In the embodiment shown in FIG. 1, burst valve 30 is a three-way burst valve. In one embodiment, burst valve 30 can be an electric operated solenoid valve. When burst valve 30 is in an energized state, testing material is delivered from burst valve 30 to sensor 40 via line 32.

Automated testing apparatus 1 also includes sensor 40, which is part of detector 50. Non-limiting examples acceptable devices suitable for use sensor 40 can include, for example solid state, catalytic bead type sensors, or the like. Detector controller 45, is in communication with sensor 40, and is operable to communicate with testing control module 70 and sensor 40. Those of ordinary skill in the art will readily recognize suitable devices for use as detector controller 45. Optional sensor diffuser 60 allows air to freely flow in and out, thereby mixing with the testing material delivered by burst valve 30, while also providing uniform access of testing material to sensor 40 and additional protection to sensor 40.

As shown in FIG. 1, testing control module 70 is in communication with burst valve assembly 31, detector 50, user interface panel 80, and remote user interface 100. In the embodiment shown in FIG. 1, testing control module 70 is also in communication with optional field user interface panel 90. Those of ordinary skill in the art will recognize that line 52 does not necessarily have to be a physical line. Therefore, any connection that allows for testing control module 70 to directly or indirectly communicate with detector 50 is acceptable. Non-limiting examples acceptable of devices suitable for use as testing control module 70 can include, for example safety certified programmable logic controllers, or the like.

Additionally, testing control module 70 can also be in communication with burst valve 30 via TCM-burst valve line 72, which allows testing control module 70 to be operable to control whether burst valve 30 is energized or de-energized. Burst valve 30 can also include solenoid 35, which determines the energized state of burst valve 30 based on the signal received from testing control module 70. Those of ordinary skill in the art will recognize that TCM-burst valve line 72 does not necessarily have to be a physical line. Therefore, any connection that allows for testing control module 70 to directly or indirectly communicate with burst valve 30 is acceptable. Testing control module 70 can accept signals from user interface panel 80, field user interface panel 90, and/or remote user interface 100 in order to initiate the testing sequence. User interface panel 80 is locally located relative to the detector. Remote user interface 100 is located remotely from the detector such that a user accessing remote user interface 100 would not be exposed to environmental conditions directly surrounding the sensor. Field user interface panel 90 is an optional panel for simplified access to the testing control module but without being located at an inconveniently remote location and without being located within the potentially hazardous area designated for monitoring by the sensor. Additionally, testing control module 70 can also collect and store diagnostic data collected during the testing sequence on internal memory. Additionally, in one embodiment, the internal memory is operable to store instructions that can be initiated through user interface panel 80 locally placed within detector housing 110, as shown in FIG. 2, or mounted (not shown) to detector housing 110.

Automated testing apparatus 1 can also include one or more user interface devices. In the embodiment shown, automated testing apparatus 1 includes user interface device panel 80. User interface panel 80 is in electronic communication with testing control module 70 and is preferably located proximate to sensor 40. This allows a user to effectively initiate the testing sequence locally as part of a troubleshooting mechanism in the event of a failure. User interface panel 80 can include local indicator lights, such as fault indicator 82, warning indicator 84, and critical indicator 86 or a warning code display. Additionally, user interface panel 80 includes local test and reset triggers 88, which in one embodiment can be buttons.

In another embodiment, automated testing apparatus 1 can include field user interface panel 90. Field user interface panel 90 is in electronic communication with testing control module 70 and is preferably located in a non-hazardous area that is away from sensor 40. Field user interface panel 90 is preferably similar to user interface panel 80, except that it is located in a location away from sensor 40. Similarly, automated testing apparatus 1 can also include remote user interface 100. Remote user interface 100 is in electronic communication with testing control module 70 and is preferably located in a non-hazardous location, for example in a control room. This placement advantageously gives an operator the ability to initiate testing sequences remotely without having to go out into the field, where the operator could be subjected to potentially hazardous conditions.

Figure 2:
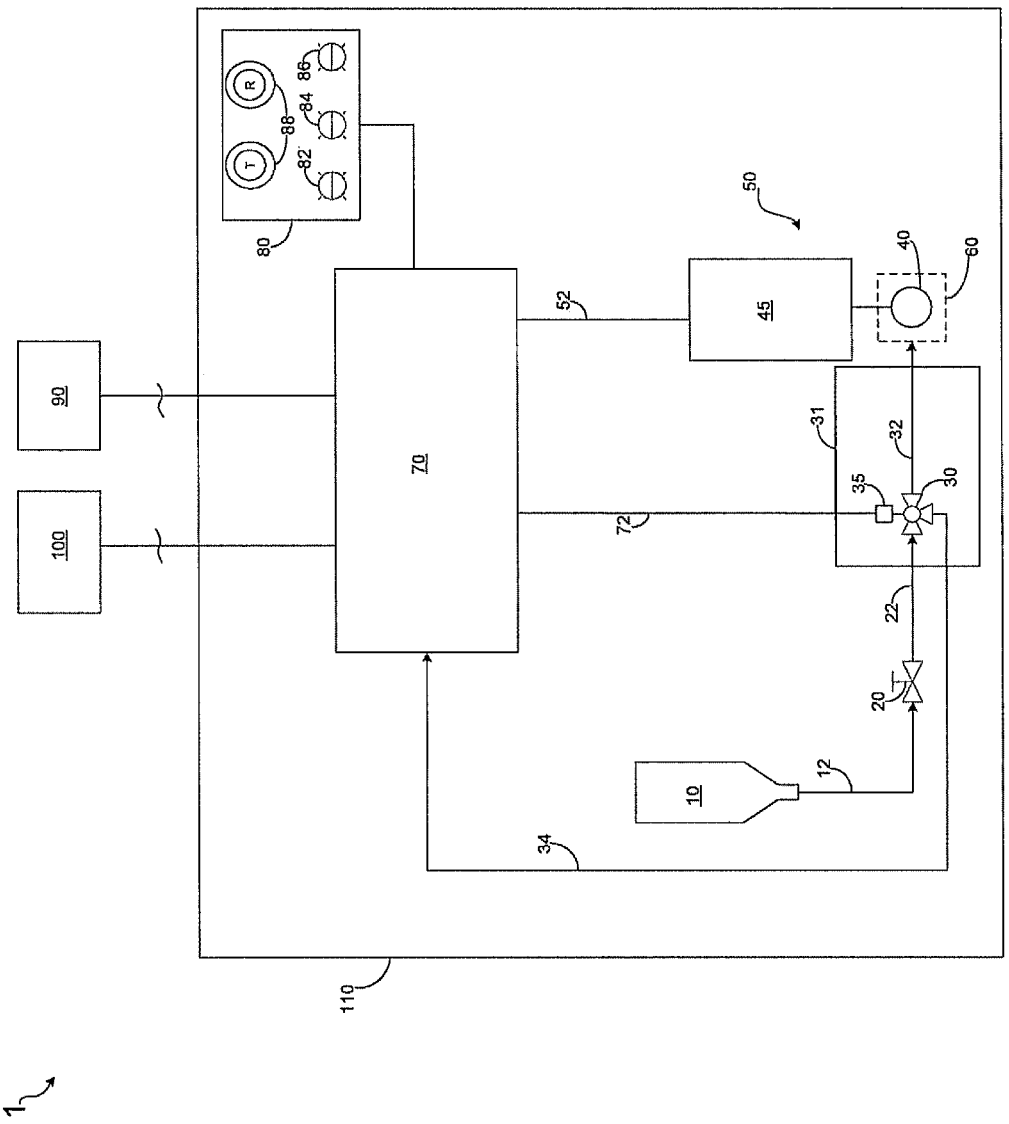
FIG. 2 is a representation of another embodiment of the present invention.

FIG. 2 shows another embodiment of the automated testing apparatus including a pressure monitoring system employing burst valve feedback line 34. An alternate embodiment shown in FIG. 2 includes a feature that, when burst valve 30 is in a non-energized state, testing material is delivered from burst valve assembly 31 to testing control module 70 via burst valve feedback line 34, thereby allowing testing control module 70 to monitor pressure within storage container 10. This provides information related to fullness of storage container and can be included in data monitored for determination of servicing of storage container 10. Advantageously, this setup provides the user with an early warning for when it is time to recharge or replace storage container 10.

Additionally, burst valve feedback line 34 can also be used to verify that burst valve 30 functions properly during sensor testing. For example, when burst valve 30 is in its de-energized state, testing control module 70 will read a relatively constant storage container pressure reading based upon the fluid pressure in burst valve feedback line 34. However, when burst valve 30 is in its energized state, testing control module 70 should experience a pressure drop for a period of time in which the testing material flows to sensor 40. Therefore, if, during this time, testing control module 70 does not experience a distinct pressure decrease, certain embodiments of the present invention include a notification signal that will alert a failure of either the pressure monitoring system (if there was a detector reading) or of burst valve 30 failing to operate (if there was no detector reading). In an additional embodiment not shown, the pressure within storage container 10 can be monitored by more conventional methods such as a gauge, which can be in communication with testing control module 70.

In another embodiment, automated testing apparatus 1 can also include detector housing 110, which is operable to provide additional protection from plant explosions, and the like. Storage container 10 can be inside or external of detector housing 110. Accessibility to storage container 10 allows maintenance or replacement of the storage container. Likewise, user interface panel 80 can be inside or outside of detector housing 110.

Figure 3:
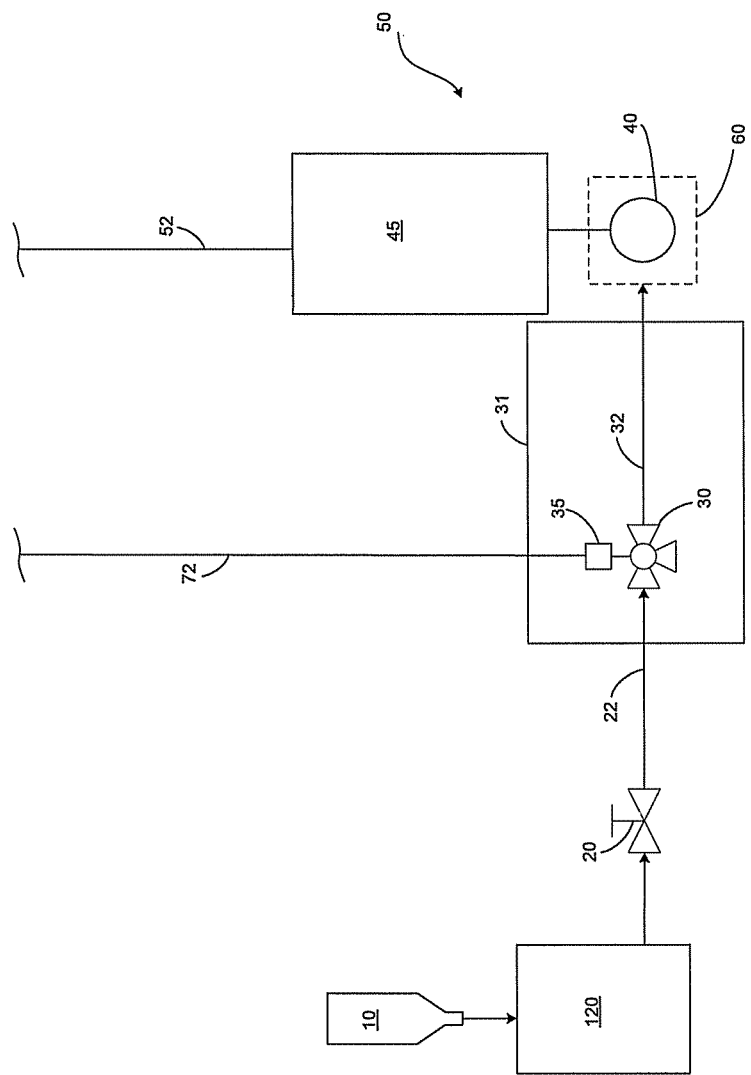
FIG. 3 is a representation of another embodiment of the present invention having a supplemental storage container.

In some embodiments, storage container 10 could have an internal pressure which is higher than what is recommended for downstream equipment. High pressure can lead to equipment failure or leaks. FIG. 3 shows an embodiment of the automated testing apparatus which is operable for alleviating higher pressures by including supplemental storage container 120. Supplemental storage container 120 allows for having storage container 10 that is under high pressure without causing unnecessary strain on the other equipment. Supplemental storage container 120 is in fluid communication with storage container 10 and burst valve assembly 31. In one embodiment, supplemental storage container 120 lowers the pressure by having an internal volume larger than the internal volume of storage container 10. In another embodiment, a lower pressure within supplemental storage container 120 is achieved by at least partially feeding the testing material of storage container 10 into supplemental storage container 120.

Figure 4:
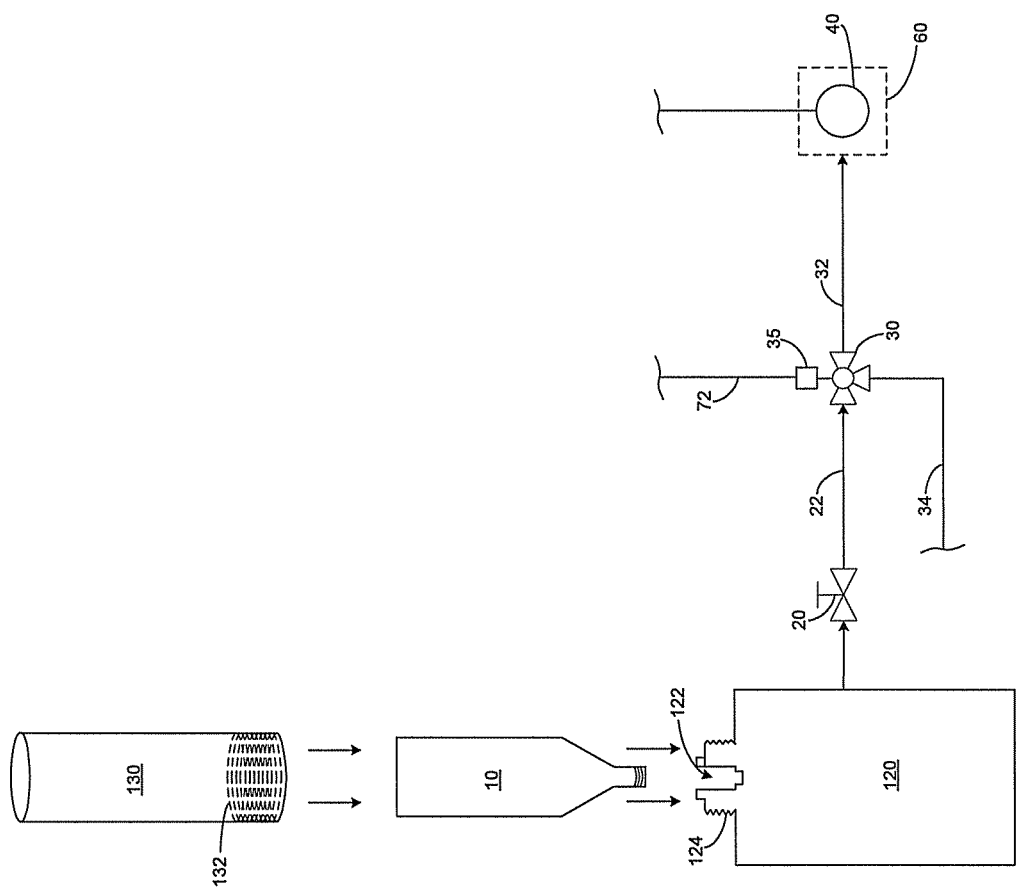
FIG. 4 is a representation of an embodiment of the supplemental storage container.

FIG. 4 shows an embodiment of the present invention with additional detail for supplemental storage container 120. In this embodiment, storage container 10 is inserted into supplemental storage container 120 at seat 122. Field connector 130 is then placed over and around storage container 10 and subsequently screwed onto supplemental storage container 120 by engaging storage container threads 124 with field connector threads 132. When field connector 130 is screwed into place, field connector 130 pushes down onto storage container 10, which in turn causes storage container 10 to fully engage with seat 122. When fully engaged, the testing material within storage container 10 flows into supplemental storage container 120. In this embodiment, supplemental storage container 120 is of a larger volume than storage container 120, which results in a lower internal pressure. In one embodiment, when field connector 130 and storage container are removed, seat 122 is returned to an isolating position via an internal spring [not shown], thereby isolating the contents of supplemental storage container 120. Those of ordinary skill in the art will recognize that there are other ways for connecting storage container 10 with supplemental storage container 120, and the present invention is intended to embrace all such alternatives. Additionally, supplemental is used as an identifier, and is not to be construed in a limiting fashion.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed.

I claim:

1. An automated testing apparatus for detection of a chemical substance, the apparatus comprising:
    (a) a detector having a sensor operable to detect the presence of a chemical substance;
    (b) a storage container for storing a testing material;
    (c) a burst valve assembly in fluid communication with the storage container, the burst valve assembly comprising a burst valve, the burst valve operable to control an amount of the testing material releasable from the storage container through the burst valve assembly such that the burst valve assembly is operable to deliver a quantity of the testing material through the burst valve assembly, the burst valve assembly being positioned in relation to the sensor such that the burst valve assembly is operable to deliver the quantity of testing material in close proximity to the sensor, such that the testing material can be detected by the sensor;
    (d) a testing control module in communication with the burst valve assembly, and the Detector, the testing control module operable to provide a signal to activate the burst valve and to initiate flow of the testing material from the storage container through the burst valve assembly;
    (e) a local user interface panel in communication with the testing control module, and proximate to the sensor so that the local user interface panel is exposed to environmental conditions at the sensor, the local user interface panel having an indicator selected from the group consisting of a failed test indicator, warning condition indicator, critical condition indicator, and combinations thereof;
    (f) a supplemental storage container in fluid communication with the storage container and the burst valve assembly, the supplemental storage container operable to reduce the pressure exerted on the burst valve assembly due to the testing material; and
    (g) a field connector, wherein the supplemental storage container further comprises outer threads and a seat, the field connector having inner threads that are operable to engage the outer threads on the supplemental storage container, such that when the inner threads engage with the outer threads, a threaded connection is formed between supplemental storage container and the field connector, wherein the threaded connection is operable to cause a downward force to be exerted on the storage container, such that the storage container engages with the seat and forms the fluid communication with the supplemental storage container.

2. The automated testing apparatus as claimed in claim 1, wherein the chemical substance is selected from the group consisting of a combustible gas, hydrogen sulfide, carbon monoxide, and combinations thereof.

3. The automated testing apparatus as claimed in claim 1, wherein the testing material is a gas when released at atmospheric conditions.

4. The automated testing apparatus as claimed in claim 1, wherein the testing material is selected from the group consisting of a combustible gas, hydrogen sulfide, carbon monoxide, and combinations thereof.

5. The automated testing apparatus as claimed in claim 1, wherein the testing control module further comprises a pressure monitoring system in communication with the burst valve assembly, wherein the pressure monitoring system is operable to monitor the pressure of the storage container.

6. The automated testing apparatus as claimed in claim 5, wherein the pressure monitoring system is in pneumatic communication with the burst valve assembly.

7. The automated testing apparatus as claimed in claim 1, further comprising a means for determining the amount of testing material within the storage container.

8. The automated testing apparatus as claimed in claim 1, wherein the testing control module further comprises internal memory, wherein the internal memory is operable to store diagnostic data.

9. The automated testing apparatus as claimed in claim 8, wherein the diagnostic data includes timestamps for each testing sequence conducted, testing sequence results, and length of time between receipt of a test result from the sensor and occurrence of a designated response, wherein the test result indicates a failure of the sensor to detect the presence of the testing material.

10. The automated testing apparatus as claimed in claim 8, further comprising a means for protecting the internal memory from dangerous conditions proximate to the sensor.

11. The automated testing apparatus as claimed in claim 1, wherein the detector is selected from the group consisting of a solid-state diffusion adsorption detector, a catalytic bead-type diffusion detector, a smoke detector, a carbon monoxide detector, or an infra-red detector.

12. The automated testing apparatus as claimed in claim 1, wherein the user interface panel is operable to allow manual operation of the testing control module.

13. The automated testing apparatus as claimed in claim 1, wherein the user interface panel is proximate to the testing control module.

14. The automated testing apparatus as claimed in claim 1, wherein the user interface panel comprises a local test function switch that is operable to initiate a testing sequence for the automated testing apparatus.

15. The automated testing apparatus as claimed in claim 1, wherein the burst valve assembly is operable to deliver the testing material to the sensor without a pump or compressed air supply.

16. The automated testing apparatus as claimed in claim 1, further comprising a sensor diffuser, wherein the sensor is disposed within the sensor diffuser, the sensor diffuser having a plurality of openings, the plurality of openings being operable to allow for air to flow through the sensor diffuser.

17. The automated testing apparatus as claimed in claim 1, wherein the burst valve includes a three-way valve, such that the testing control module is in fluid communication with the burst valve.

18. The automated testing apparatus as claimed in claim 1, further comprising a TCM-burst valve line in communication with the testing control module and the burst valve assembly, the TCM-burst valve line operable to send a signal from the testing control module to the burst valve assembly to change a state of the burst valve.

19. The automated testing apparatus as claimed in claim 1, wherein the supplemental storage container has an internal volume greater than the internal volume of the storage container.

20. An automated testing apparatus for detection of a chemical substance, the apparatus comprising:
(a) a detector having a sensor operable to detect the presence of a chemical substance;
(b) a storage container for storing a testing material;
(c) a burst valve assembly in fluid communication with the storage container, the burst valve assembly comprising a three-way burst valve, the three-way burst valve operable to control an amount of the testing material releasable from the storage container through the burst valve assembly such that the burst valve assembly is operable to deliver a quantity of the testing material through the burst valve assembly, the burst valve assembly being positioned in relation to the sensor such that the burst valve assembly is operable to deliver the quantity of testing material in close proximity to the sensor, such that the testing material can be detected by the sensor;
(d) a testing control module in communication with the burst valve assembly and the detector, and in fluid communication with the three-way burst valve so that the testing control module can monitor pressure within the storage container, the testing control module operable to provide a signal to activate the three-way burst valve and to initiate flow of the testing material from the storage container through the burst valve assembly;
(e) a remote user interface remotely located from the detector so that the remote user interface is not exposed to environmental conditions at the detector, the remote user interface in communication with the testing control module, wherein the remote user interface is operable to receive a detection signal from the testing control module and output a discernible signal that is operable to indicate whether the sensor is functioning;
(f) a supplemental storage container in fluid communication with the storage container and the burst valve assembly, the supplemental storage container operable to reduce the pressure exerted on the burst valve assembly due to the testing material; and
(g) a field connector, wherein the supplemental storage container further comprises outer threads and a seat, the field connector having inner threads that are operable to engage the outer threads on the supplemental storage container, such that when the inner threads engage with the outer threads, a threaded connection is formed between supplemental storage container and the field connector, wherein the threaded connection is operable to cause a downward force to be exerted on the storage container, such that the storage container engages with the seat and forms the fluid communication with the supplemental storage container.

21. The automated testing apparatus as claimed in claim 20, wherein the remote user interface comprises:
an input/output device operable to interact with a user;
a computer defining a signal processing device having non-transitory computer memory, the computer in electronic communication with the input/output device and die testing control module, the signal processing device operable to receive and transmit instructions between the input/output device and the testing control module;
a program product stored in memory and operable on the signal processing device, the program product in electronic communication with the signal processing device, the program product composed of instructions executable for initiating a testing sequence, wherein the testing sequence includes the steps of:
delivering the testing material through the burst valve assembly in close proximity to the sensor;
sensing the presence of the testing material by the sensor; and
receiving a signal from the sensor to the testing control module indicating whether the sensor detected the presence of the testing material.

22. The automated testing apparatus as claimed in claim 21, wherein the testing control module is operable to store diagnostic data from the testing sequence, wherein the diagnostic data includes timestamps for each testing sequence conducted and testing sequence results.

23. The automated testing apparatus as claimed in claim 22, wherein the diagnostic data further includes length of time between receipt of a test result from the sensor and occurrence of a designated response, wherein the test result indicates a failure of the sensor to detect the presence of the testing material.

24. The automated testing apparatus as claimed in claim 20, wherein the remote user interface is located within a control room, such that the remote user interface can be accessed in a location away from the chemical substance.

25. An automated testing apparatus for detection of a chemical substance, the apparatus comprising:
(a) a detector having a sensor operable to detect the presence of a chemical substance;
(b) a storage container for storing a testing material;
(c) a burst valve assembly in fluid communication with the storage container, the burst valve assembly comprising a burst valve, the burst valve operable to control an amount of the testing material releasable from the storage container through the burst valve assembly such that the burst valve assembly is operable to deliver a quantity of the testing material through the burst valve assembly, the burst valve assembly being positioned in relation to the sensor such that the burst valve assembly is operable to deliver the quantity of testing material in close proximity to the sensor, such that the testing material can be detected by the sensor;
(d) a testing control module in communication with the burst valve assembly, and the detector the testing control module operable to provide a signal to activate the burst valve and to initiate flow of the testing material from the storage container through the burst valve assembly; and
(e) a remote user interface remotely located from the detector, the remote user interface in communication with the testing control module, wherein the remote user interface is operable to receive a detection signal from the testing control module and output a discernible signal that is operable to indicate whether the sensor is functioning;
(f) a supplemental storage container in fluid communication with the storage container and the burst valve assembly, the supplemental storage container operable to reduce the pressure exerted on the burst valve assembly due to the testing material; and
(g) a field connector, wherein the supplemental storage container further comprises outer threads and a seat, the field connector having inner threads that are operable to engage the outer threads on the supplemental storage container, such that when the inner threads engage with the outer threads, a threaded connection is formed between supplemental storage container and the field connector, wherein the threaded connection is operable to cause a downward force to be exerted on the storage container, such that the storage container engages with the seat and forms the fluid communication with the supplemental storage container.

26. An automated testing apparatus for detection of a chemical substance, the apparatus comprising:
(a) a detector having a sensor operable to detect the presence o a chemical substance;
(b) a storage container for storing a testing material;
(c) a burst valve assembly in fluid communication with the storage container, the burst valve assembly comprising a burst valve, the burst valve operable to control an amount of the testing material releasable from the storage container through the burst valve assembly such that the burst valve assembly is operable to deliver a quantity of the testing material through the burst valve assembly, the burst valve assembly being positioned in relation to the sensor such that the burst valve assembly is operable to deliver the quantity of testing material in close proximity to the sensor, such that the testing material can be detected by the sensor;
(d) a testing control module in communication with the burst valve assembly and the detector, the testing control module operable to provide a signal to activate the burst valve and to initiate flow of the testing material from the storage container through the burst valve assembly;
(e) a local user interface panel in communication with the resting control module, and proximate to the sensor so that the local user interface, panel is exposed to environmental conditions at the sensor, the local user interface panel having an indicator selected from the group consisting of a failed test indicator, warning condition indicator, critical condition indicator, and combinations thereof;
(f) means for measuring the pressure of the testing material within the storage container; and
(g) means for calculating the amount of testing material flowing through the burst valve assembly based on the amount of time the burst valve is in an open position and the pressure difference of the storage container between a closed position and the open position of the burst valve.

* * * * *

UNITED STATES PATENT AND TRADEMARK OFFICE
CERTIFICATE OF CORRECTION

| | | |
|---|---|---|
| PATENT NO. | : 9,110,041 B2 | Page 1 of 1 |
| APPLICATION NO. | : 13/198155 | |
| DATED | : August 18, 2015 | |
| INVENTOR(S) | : Patrick S. Flanders | |

It is certified that error appears in the above-identified patent and that said Letters Patent is hereby corrected as shown below:

Claims

In Column 10, Line 24, Claim 1, the sixth word appears as "Detector" and should read --detector--.

In Column 12, Line 50, Claim 21, the first word appears as "die" and should read --the--.

In Column 14, Line 35, Claim 26, the first word appears as "resting" and should read --testing--.

In Column 14, Line 36, Claim 26, the fifth word appears as "interface," and should read --interface--.

Signed and Sealed this
Twenty-second Day of December, 2015

Michelle K. Lee
*Director of the United States Patent and Trademark Office*